United States Patent [19]

Kamiya et al.

[11] 4,077,965
[45] Mar. 7, 1978

[54] AMINOALKYL- OR HYDROXYALKYL-SUBSTITUTED THIADIAZOLE DERIVATIVES

[75] Inventors: Takashi Kamiya, Suita; Kunihiko Tanaka; Tsutomu Teraji, both of Toyonaka; Keiji Hemmi, Kyoto, all of Japan

[73] Assignee: Fujisawa Pharmaceutical Co., Ltd., Osaka, Japan

[21] Appl. No.: 509,905

[22] Filed: Sep. 27, 1974

Related U.S. Application Data

[63] Continuation-in-part of Ser. No. 454,805, Mar. 26, 1974, abandoned.

[30] Foreign Application Priority Data

Oct. 13, 1973  Japan ................................ 48-115013

[51] Int. Cl.² ........................................... C07D 285/12
[52] U.S. Cl. ............................. 260/302 SD; 544/24; 544/25; 544/26; 544/27
[58] Field of Search .................................. 260/302 SD

[56] References Cited

FOREIGN PATENT DOCUMENTS 7,207,370  10/1969  Japan ............................ 260/302 SD

OTHER PUBLICATIONS

Rodd "Chemistry of Carbon Compounds" vol. IV, part A, Heterocyclic Compounds pp. 476–477, E. I. Sevler, (1957).
Girard, Comptes Rendus Acad. des Sciences, de Paris, Tome 225, pp. 458–460 (1947).

Primary Examiner—Donald G. Daus
Assistant Examiner—D. B. Springer
Attorney, Agent, or Firm—Dayton R. Stemple, Jr.

[57]  ABSTRACT

Compounds of the formula

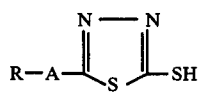

and its salts, wherein A is lower alkylene, and R is optionally acyl or lower alkoxy carbonyl substituted amino or optionally acyl substituted hydroxy. The compounds are useful as intermediates in making cephalosporin derivatives.

11 Claims, No Drawings

AMINOALKYL- OR HYDROXYALKYL-SUBSTITUTED THIADIAZOLE DERIVATIVES

This application is a continuation-in-part of our patent application Ser. No. 454,805, filed Mar. 26, 1974, abandoned.

This invention relates to new cephalosporanic acid derivatives which possess an antibacterial activity, processes for preparing the same, pharmaceutical compositions thereof, and new intermediates for the preparation of said cephalosporanic acid derivatives.

The cephalosporanic acid derivatives of this invention can be represented by the following general formula I:

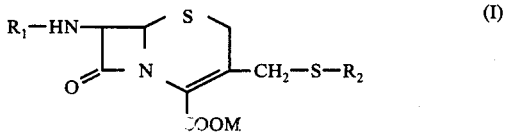

wherein $R_1$ is hydrogen atom or acyl group, $R_2$ is aminoalkyl-, acylaminoalkyl- or hydroxyalkyl- substituted, N- or N and S- containing heterocyclic group and M is hydrogen atom or nontoxic, pharmaceutically acceptable cation.

The term "acyl" represented by $R_1$ means an acyl group derivable from an organic carboxylic acid, such as a saturated or unsaturated aliphatic carboxylic acid in which the carbon chain may be straight or branched or cyclic and may be interrupted by an oxygen atom or a sulfur atom; aromatic group substituted aliphatic carboxylic acid, aromatic group-oxy substituted aliphatic carboxylic acid, aromatic group-thio substituted aliphatic carboxylic acid, heterocyclic group substituted aliphatic carboxylic acid, heterocyclic-oxy substituted aliphatic carboxylic acid or heterocyclic-thio substituted aliphatic carboxylic acid in which the aliphatic carboxylic acid mentioned above is combined with an aromatic hydrocarbon residue or a heterocyclic group via or not an oxygen atom or a sulfur atom; aromatic carboxylic acid, heterocyclic carboxylic acid, or the like. Said aliphatic carboxylic acid may be formic acid, acetic acid, propionic acid, butyric acid, isobutyric acid, pentanoic acid, isopentanoic acid, pivalic acid, hexanoic acid, cyclohexane carboxylic acid, acrylic acid, crotonic acid, cyclopentylacetic acid, cyclohexylacetic acid, cycloheptylacetic acid, cyclohexylpropionic acid, cyclohexenylacetic acid, cyclohexadienylacetic acid, methoxyacetic acid, cyclohexyloxyacetic acid, methylthioacetic acid, or the like. The aromatic hydrocarbon residue (i.e. aromatic group) included in the above organic carboxylic acids may be phenyl, naphthyl, tolyl, xylyl, mesityl, cumenyl, or the like. The heterocyclic group included in the above organic carboxylic acids may be a residue of saturated or unsaturated, and mono- or poly-cyclic compound including one or more hetero atoms, such as furan, thiophene, pyrrole, pyrazole, imidazole, triazole, thiazole, isothiazole, oxazole, isoxazole, thiadiazole, oxadiazole, thiatriazole, oxatriazole, tetrazole, pyridine, pyrazine, pyrimidine, pyridazine, benzothiophene, benzofuran, indole, indazole, benzimidazole, benzothiazole, benzothiadiazole, benzoxazole, purine, quinoline, isoquinoline, phthalazine, naphthyridine, quinoxaline, quinazoline, pyrrolidine, imidazolidine, piperidine, piperazine, or the like. The aliphatic residues, aromatic residues and heterocyclic residues of these organic carboxylic acids may have one or more substituents inert to the reaction of the process in this invention, such as halogen, hydroxy, mercapto, carboxy, alkyl, alkoxy, alkylthio, nitro, sulfo, amino, alkylamino, dialkylamino, cyano, alkanoyl, aralkanoyl, aralkanoyloxy, arylcarbonyloxy, and the like. Among these substituents, the hydroxy, sulfo, mercapto, carboxy and amino group may be protected respectively by a conventional protecting group.

The term "aminoalkyl" which is a substituent of the N- or N and S- containing heterocyclic group means aminomethyl, 1-aminoethyl, 2-aminoethyl, 1-aminopropyl, 2-aminopropyl, 3-aminopropyl, 1-aminobutyl, 2-aminobutyl, 3-aminobutyl, 4-aminobutyl, 5-aminopentyl, 6-aminohexyl, 2-aminoisopropyl, 3-aminoisobutyl, and the like.

The term "acylaminoalkyl" which is a substituent of the N- or N and S- containing heterocyclic group means an acyl substituted aminoalkyl group in which the aminoalkyl group is referred to the one as mentioned above and the acyl group is the same as th one represented by $R_1$, and includes an alkoxycarbonyl substituted aminoalkyl group in which the alkoxycarbonyl group means methoxycarbonyl, ethoxycarbonyl, propoxycarbonyl, isopropoxycarbonyl, butoxycarbonyl, isobutoxycarbonyl, tert-butoxy-carbonyl, etc.; an alkanesulfonyl substituted aminoalkyl group in which the alkanesulfonyl group means methanesulfonyl, ethanesulfonyl, propanesulfonyl, isopropanesulfonyl, butanesulfonyl, isobutanesulfonyl, tert-butanesulfonyl, pentanesulfonyl, hexanesulfonyl, etc.; an N-alkylcarbamoyl substituted aminoalkyl group in which the N-alkylcarbamoyl group means N-methylcarbamoyl, N-ethylcarbamoyl, N-propylcarbamoyl, etc.; a 1-guanidinocarbonyl substituted aminoalkyl group, and the like.

The term "hydroxyalkyl" which is a substituent of the N- or N and S- containing heterocyclic group means hydroxymethyl, 1-hydroxyethyl, 2-hydroxyethyl, 1-hydroxypropyl, 2-hydroxypropyl, 3-hydroxypropyl, 1-hydroxybutyl, 2-hydroxybutyl, 3-hydroxybutyl, 4-hydroxybutyl, 5-hydroxypentyl, 6-hydroxyhexyl, 2-hydroxyisopropyl, 3-hydroxyisobutyl, and the like.

The term "N- containing heterocyclic group" means a residue of a mono- or poly-cyclic compound containing one or more nitrogen atoms such as pyrrole, imidazole, pyrazole, triazole, 1H-tetrazole, 2H-tetrazole, pyridine, pyrazine, pyrimidine, pyridazine, indolizine, isoindole, 3H-indole, indole, 1H-indazole, purine, quinoline, isoquinoline, phthalazine, naphthyridine, quinoxaline, quinazoline, cinnoline, pteridine, β-carboline, benzimidazole, and the like.

The term "N and S- containing heterocyclic group" means a residue of a mono- or poly-cyclic compound containing one or more nitrogen atoms and sulfur atoms such as thiazole, isothiazole, 1,3,4-thiadiazole, 1,2,5-thiadiazole, 1,2,4-thiadiazole, benzothiazole, and the like.

The term "nontoxic, pharmaceutically acceptable cation" means an alkali metal such as sodium, potassium, and the like.

The objective cephalosporanic acid derivatives (I) may be prepared by reacting 7-substituted cephalosporanic acids of formula II:

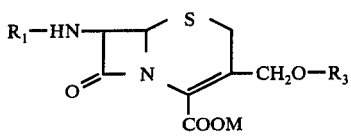

wherein $R_3$ is alkanoyl group, and $R_1$ and M are as defined above, with an aminoalkyl-, acylaminoalkyl- or hydroxyalkyl-substituted, N- or N and S- con containing heterocyclic thiol compounds of formula III:

wherein $R_2$ is as defined above, or a alkali metal salt thereof.

The term "alkanoyl" represented by $R_3$ in the formula (II) means acetyl, propionyl, butylyl, pentanoyl, hexanoyl, and the like.

The alkali metal salt of the thiol compound (III) may be sodium salt, potassium salt, or the like.

The reaction of the 7-substituted cephalosporanic acids (II) with the thiol compounds (III) or the alkali metal salts thereof may be carried out in a solvent such as water, acetone, chloroform, nitrobenzene, dimethylformamide, methanol, ethanol dimethylsulfoxide, or any other organic solvents inert to the reaction, preferably in a strongly polar solvent. Among the solvents, hydrophilic solvents may be used in a mixture with water. The reaction is preferably carried out in around neutral medium. When the compound (II) or the thiol compound (III) is used in a free form, the reaction is preferably conducted in the presence of a base such as alkali metal hydroxide, alkali metal carbonate, alkali metal bicarbonate, trialkylamine, and the like. The reaction temperature is not restrictive, and the reaction is usually carried out at room temperature or under warming. The reaction product can be isolated from the reaction mixture by conventional methods.

When the reaction is carried out by applying the compound (II) having amino group for $R_1$—HN— or the thiol compound (III) having aminoalkyl substituted, N- or N and S-containing heterocyclic group for $R_2$, these free amino groups may be protected by conventional protecting groups. In this case, the amino protecting group may be removed from the reaction product, if necessary, and this process is also included in the scope of the present invention.

The removing reaction of the amino protecting group may be carried out by a conventional method such as decomposition by acid, catalytic reduction, and the like, which is selected according to the kind of the protecting group on the amino group. The decomposition by acid is one of the most suitable method and may be applied for the removal of the substituents such as benzyloxycarbonyl, substituted benzyloxycarbonyl, alkoxycarbonyl, substituted alkoxycarbonyl, aralkoxycarbonyl, adamantyloxycarbonyl, trityl, substituted phenylthio, substituted aralkylidene, substituted alkylidene, substituted cycloalkylidene, and the like. The acid applied in the above reaction is selected according to the kind of the amino protecting group, and the suitable acids are formic acid, trifluoroacetic acid, and the like, which are easily evaporated under reduced pressure. When the decomposition by acid is carried out in a solvent, a hydrophilic organic solvent, water or a mixture thereof is occasionally used as a solvent. The catalytic reduction may be applied for the removal of the amino protecting group such as benzyloxycarbonyl, substituted benzyloxycarbonyl, 2-pyridylmethoxycarbonyl, and the like. The suitable catalyst is palladium, and the other catalysts conventionally applied for the catalytic reduction may be also used. The trifluoroacetyl group may be removed by treating the reaction product with water, and the halogen-substituted alkoxycarbonyl group and 8-quinolyloxycarbonyl group may be removed by treating the reaction product with a heavy metal such as copper, zinc, and the like. The removing reaction of the amino protecting group may be carried out without the isolation and the purification of the reaction product from the reaction medium. Some of the object compounds, 7-acylamino-3-aminoalkyl-, acylaminoalkyl- or hydroxyalkyl-substituted, N- or N and S-containing heterocyclic thiomethyl-3-cephem-4-carboxylic acids of formula I':

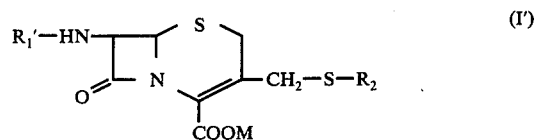

wherein $R_1'$ is acyl group, and $R_2$ and M are as defined above, may be prepared by reacting compounds of formula IV:

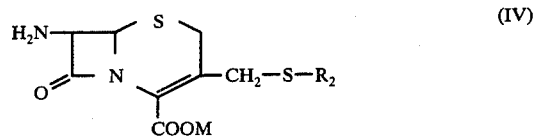

wherein $R_2$ and M are as defined above, or their derivatives at the amino group and/or the carboxy group, with organic carboxylic acids of formula V:

wherein $R_1'$ is as defined above, or their reactive derivatives of the carboxy group.

The derivative at the carboxy group of the compound (IV) may be a salt such as magnesium salt, calcium salt, triethylamine salt, etc.; an ester such as methyl ester, ethyl ester, propyl ester, butyl ester, pentyl ester, trimethylsilyl ester, 2-mesylethyl ester, 2-iodethyl ester, 2,2,2-trichloroethyl ester, benzyl ester, 4-methoxybenzyl ester, 4-nitrobenzyl ester, phenacyl ester, phenethyl ester, trityl ester, diphenylmethyl ester, bis(methoxyphenyl)methyl ester, 3,4-dimethoxybenzyl ester, (1-cyclopropyl)ethyl ester, ethynyl ester, 4-hydroxy-3,5-di-tert-butylbenzyl ester, etc.; an activated amide; an acid anhydride; an acid halide, or the like.

The derivative at the amino group of the compound (IV) may be the reaction product of the compound (IV) and a silyl compound such as bis(trimethylsilyl)acetamido, or the like.

The reactive derivative at the carboxy group of the organic carboxylic acid (V) may be an acid halide, an acid anhydride, an activated amide, an activated ester, or the like. The suitable examples may be an acid chloride, an acid azido; a mixed acid anhydride with an acid such as dialkylphosphoric acid, phenylphosphoric acid, diphenylphosphoric acid, dibenzylphosphoric acid, halogenated phosphoric acid, dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid) or aromatic carboxylic acid (e.g. benzoic acid), or a symmetrical acid anhydride; an acid amide with imidazole, 4-substituted imidazole, dimethylpyrazole, triazole or tetrazole; or an ester (e.g. cyanomethyl ester, methoxymethyl ester, vinyl ester, propargyl ester, p-nitrophenyl ester, 2,4-dinitrophenyl ester, trichlorophenyl ester, pentachlorophenyl ester, methanesulfonylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or an ester with N, N-dimethylhydroxylamine, 1-hydroxy-2-(1H)-pyridone, N-hydroxysuccinimide or N-hydroxyphthalimide), or the like. The suitable derivative can be optionally selected from them according to the kind of the organic carboxylic acid (V) to be used practically.

The reaction is usually carried out in a solvent such as acetone, dioxan, acetonitrile, chloroform, methylene chloride, ethylene chloride, tetrahydrofuran, ethyl acetate, dimethylformamide, pyridine or any other organic solvent inert to the reaction. Among these solvents, hydrophilic solvents may be used in a mixture with water.

When the organic carboxylic acid (V) is used in a form of the free acid or its salt in this reaction, the reaction is preferably carried out in the presence of a condensing agent such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonyldi(2-methylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, 2-ethyl-7-hydroxybenzisoxazolium salt, 2-ethyl-5-(m-sulfophenyl)isoxazolium hydroxide intermolecular salt, (chloromethylene)dimethylammonium chloride, and the like. The salt of the organic carboxylic acid (V) may be an alkali metal salt, an alkaline earth metal salt, an ammonium salt, a salt with an organic base such as trimethylamine, dicyclohexylamine or the like.

The reaction may be carried out in the presence of a base such as alkali metal bicarbonate, trialkylamine, N,N-dialkylbenzylamine, pyridine, and the like. When the base or the condensing agent is in liquid, it can be used also as a solvent. The reaction temperature is not restrictive, and the reaction is usually carried out under cooling or at room temperature.

Some kinds of the amino protecting groups on the aminoalkyl-substituted N- or N and S-containing heterocyclic group represented by the symbol $R_2$ in the compound (IV), may be removed in the course of the reaction or the post-treatment to give directly the object compound (I') having a free amino group.

When the reaction product have the amino protecting group, the amino protecting group may be removed from the reaction product, when desired, by applying a suitable removing reaction as mentioned above.

Furthermore, some of the objective compounds, 7-acylamino-3-acylaminoalkyl substituted, N- or N and S-containing heterocyclic thiomethyl-3-cephem-4-carboxylic acids of formula I'':

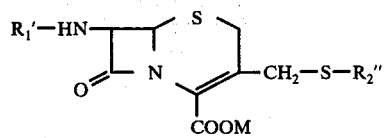

wherein $R_1'$ and M are as defined above and $R_2'$ is acylaminoalkyl substituted, N- or N and S-containing heterocyclic group, may be prepared by acylating 7-acylamino-3-aminoalkyl substituted, N- or N and S-containing heterocyclic thiomethyl-3-cephem-4-carboxylic acids of formula I''':

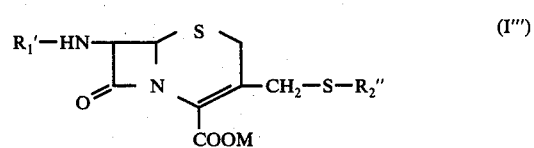

(I''')

wherein $R_1'$ and M are as defined above, and $R_2''$ is aminoalkyl substituted, N- or N and S-containing heterocyclic group, or their derivatives at the carboxy group. The derivatives at the carboxy group of the compounds (I''') are as mentioned above.

The acylating agent applied in the reaction may be the organic carboxylic acids (V) mentioned above, organic sulfonic acids, organic carbonic acid esters or organic carbamic acids, or thio acids thereof, or reactive derivatives thereof, in which the reactive derivatives are as mentioned above, and the organic sulfonic acids, organic carbonic acid esters, organic carbamic acids and thio acids thereof may have the same organic residues as those of the organic carboxylic acids (V).

The acylating reaction of the compounds (I''') may be carried out in a solvent such as benzene, ether, acetone, dioxane, acetonitrile, chloroform, methylene chloride, tetrahydrofuran, ethyl acetate, dimethylformamido, pyridine, or any other organic solvents inert to the acylating reaction. Among the solvents, hydrophilic solvents may be used in a mixture with water. The reaction temperature is not restrictive, and the reaction is usually carried out at room temperature or under warming. The reaction may be carried out in the presence of the condensing agent or the base as mentioned above.

All the reactants to be employed in the various processes of the present invention may be commercially available or be prepared by conventional methods well known to the art or by a variety of analogous methods applicable to production of such reactants, some of which are mentioned below.

In accordance with the present invention, a precipitate which forms during the reaction is separated from the reaction mixture by methods commonly used for this purpose, and the resulting reaction product may be subjected to routinely used purification procedures, for instance, to recrystallization from an appropriate solvent or a mixture of such solvents.

The compounds of the present invention may be converted by conventional methods of forming salts from acids into their pharmaceutically acceptable, substantially non-toxic salts, for instance, by reaction with an alkali metal hydroxide, an alkali metal bicarbonate, an alkali metal carbonate, or an organic base, sodium salt being preferred. The preferred method of preparing the salts consists in dissolving the acid in a solvent wherein the salt is insoluble and then adding a solution of the salt-forming compound or the base thereto. Thereby the salt precipitates from the reaction mixture.

The compounds of the present invention exhibit a high antibacterial activity and inhibit the growth of a number of microorganisms including Gram-positive and Gram-negative bacteria. For therapeutic administration the cephalosporin compounds according to the present invention are used in the form of pharmaceutical preparation which contain said compounds in admixture with a pharmaceutically acceptable organic or inorganic solid or liquid excipient suitable for oral or parenteral administration. The pharmaceutical preparations may be in solid form such as capsules, tablets, or dragees, or in liquid form such as solutions, suspensions, or emulsions. If desired, there may be included in the above preparations auxiliary substances, stabilizing agents, wetting or emulsifying agents, buffers and other commonly used additives.

While the dosage of the compounds will vary from and also depend upon the age and condition of the patient, an average single dose of about 100 mg., 250 mg., and 500 mg. of the compounds according to the present invention has proved to be effective in treating diseases caused by bacterial infection. In general amounts between 10 mg. and about 1000 mg. or even more may be administered.

Among the reagents to be used in the processes of the present invention, some of the compounds (III) are new compounds and can be represented by the formula:

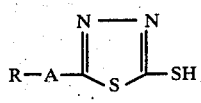
(Ia)

wherein A is lower alkylene and R is amino which may be substituted with acyl or lower alkoxycarbonyl, or hydroxy which may be substituted with acyl.

As used herein, the term "lower alkylene" means straight or branched carbon chain having up to six carbon atoms, and includes methylene, ethylene, trimethylene, propylene, tetramethylene, pentamethylene, hexamethylene and the like; "acyl" includes lower alkanoyl having up to six carbon atoms (e.g. formyl, acetyl, propionyl, butyryl, t-butyryl, valeryl or caproyl), aroyl (e.g. benzoyl, toluoyl or xyloyl) and heterocyclic-carbonyl (e.g. nicotinoyl, tenoyl or furoyl); "lower alkoxycarbonyl" means one having up to seven carbon atoms and includes methoxycarbonyl, ethoxycarbonyl, propoxycarbonyl, butoxycarbonyl, t-butoxycarbonyl, pentyloxycarbonyl, hexyoxycarbonyl and the like; and the salts of the compound (Ia) are acid addition salts, i.e., organic and inorganic acid addition salts (e.g. hydrochloride, hydrobromide, sulfate, nitrate, phosphate, tartrate, citrate or the like) and salts with a base such as alkali metal (e.g. sodium or potassium) or alkaline earth metal (e.g. magnesium or calcium) and the like.

According to the present invention, the 5-substituted lower alkyl-1,3,4-thiadiazole-2-thiol compound (Ia) can be prepared by reacting a salt or an ester of dithiocarbazic acid of the formula:

R—A—CO—NH—NH—CSSH (IIa)

wherein A and R are each as defined above, with a dehydrating agent to give the compound of the formula:

(IIIa)

wherein A is as defined above and Ra is amino which may be substituted with acyl, or hydroxy, and when desired, followed by hydrolysing the resultant compound (IIIa) wherein Ra is amino which is substituted with acyl to give the compound of the formula:

(IVa)

wherein A is as defined above, or by reacting the resultant compound (IIIa) wherein Ra is amino, with a reagent being capable of introducing a lower alkoxycarbonyl group on the amino group, to give the compound of the formula:

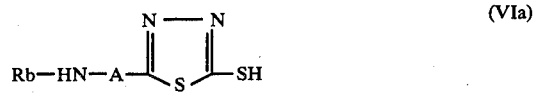
(VIa)

wherein A is as defined above and Rb is lower alkoxycarbonyl, or by acylating the resultant compound (IIIa) wherein Ra is hydroxy with an acylating agent of the formula:

Rc — OH (VIIa)

wherein Rc is acyl, or its functional derivative at the carboxy group to give the compound of the formula:

(VIIIa)

wherein A and Rc are each as defined above.

The starting compound (IIa) of the present invention can be prepared, for example, by reacting the compound of the formula:

R—CO—NH—NH$_2$ wherein R is as defined above, with carbon disulfide in the presence of a base.

In the process of the present invention, is first conducted the ring-closure of the dithiocarbazic acid (IIa) by reacting the salt or ester of the compound (IIa) with the dehydrating agent to give the compound (IIIa).

The dehydrating agent to be used in the ring-closure of the present invention means an inorganic acid having dehydrative activity such as a strong inorganic acid (e.g. sulfuric acid, phosphoric acid, polyphosphoric acid and the like).

In carrying out the process of this invention, the salt of the compound (IIa) may be a salt with an alkali metal such as sodium, potassium, and the like, a salt with ammonia, hydrazine, an organic base such as alkylamine (e.g. mono-, di- or tri-methylamine, mono-, di- or tri-ethylamine, mono-, di- or tri-propylamine, methylethylamine, diethylpropylamine or dimethylisopropylamine),aralkylamine (e.g. benzylamine), arylamine (e.g. aniline) or heterocyclic amine (e.g. pyridine, α-, β- or γ-picoline, pyrrolidine, N-methylpyrrolidine, imidazolidine, piperidine, N-methylpiperidine or piperazine) and the like, and the ester of the compound (IIa) may be alkyl or substituted alkyl ester such as methyl, ethyl, propyl, isopropyl, butyl, isobutyl, t-butyl, pentyl, hexyl or (mono-, di- or tri-)halogen-substituted lower alkyl (e.g. 1,2-dichloroethyl or 2,2,2-trichloroethyl) or ar(lower)alkyl ester such as benzyl or phenethyl and the like.

In carrying out the ring-closure, it is desirable to use the dehydrating agent in a high concentration or in possibly anhydrous condition. The reaction temperature is not critical and usually carried out advantageously at a temperature from under cooling to at room temperature. The reaction is usually carried out in a solvent and any solvent inert to this reaction, such as acetic acid or ethyl acetate, can be used. The dehydrating agent when it is in liquid can be also employed as solvent. When an organic solvent is used in this reaction, it is preferable that such solvent is to be as anhydrous as possible.

In case of using, as starting compound, the compound (IIa) wherein R is amino which is substituted with lower alkoxycarbonyl or hydroxy which is substituted with acyl, there may sometime be obtained the compound of the formula:

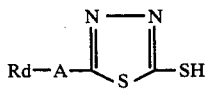

wherein A is as defined above and Rd is amino or hydroxy, due to the elimination of the substituent on the amino or hydroxy group in the course of the reaction, depending on a reaction condition practically undertaken. This process is also included within the scope of the present invention.

Thus obtained compound (IIIa) is further subjected to the conversions as illustrated by the following formulae and also can be used for the following reaction without separation and purification from the reaction mixture obtained in the ring-closure.

Conversion 1 (Hydrolysis)

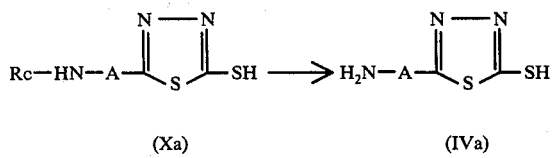

(Xa)          (IVa)

wherein A and Rc are each as defined above.

The compound (Xa) used as starting compound in the conversion 1 can be referred to the compound (IIIa) wherein Ra is amino which is substituted with acyl. The conversion is conducted by hydrolysing the compound (Xa), wherby the acylamino group is converted into the amino group. The hydrolysis is advantageously carried out by heating the compound (Xa) or its salt with a base in an aqueous solution of a base such as sodium hydroxide, potassium hydroxide, sodium carbonate, potassium carbonate or of an inorganic acid such as sulfuric acid or hydrochloric acid to give the compound (IV).

Conversion 2

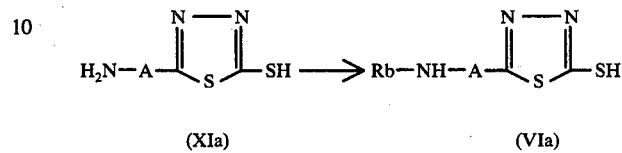

(XIa)          (VIa)

wherein A and Rb are each as defined above.

The compound (XIa) used as starting compound in the conversion 2 can be referred to the compound (IIIa) wherein Ra is amino.

The conversion 2 is carried out by reacting the compound (XIa) or its salt with the reagent being capable of introducing a lower alkoxycarbonyl group on the amino group to give the compound (IVa), whereby the amino group is converted into the lower alkoxycarbonylamino group.

As the reagent being capable of introducing a lower alkoxycarbonyl group on the amino group to be used in the conversion 2, may be alkoxycarbonyl azide of the formula: $Rb-N_3$ (V) wherein Rb is as defined above, lower alkyl chloroformate, dimethyl 2-lower alkoxycarbonyloxyimino malonate and other reagent usable conventionally for converting an amino group to a lower alkoxycarbonylamino group by introducing a lower alkoxycarbonyl group on an amino group.

The reaction of the conversion 2 is carried out preferable in the presence of a base such as triethylamine or tetramethylguanidine and usually in a mixed solvent of water and a solvent miscible with water. The reaction temperature may be suitably selected depending on the kind of the starting compound and the reagent to be used practically.

Conversion 3 (Acylation)

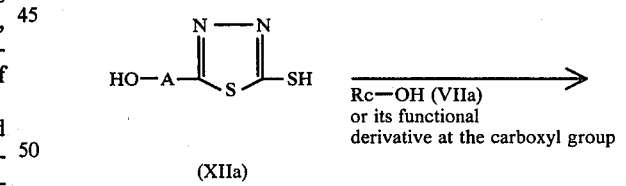

(XIIa)

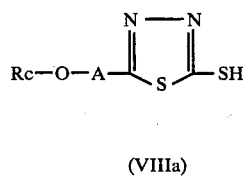

(VIIIa)

wherein A and Rc are each as defined above.

The compound (XIIa) used as starting compound in the conversion 3 can be referred to the compound (IIIa) wherein Ra is hydroxy.

The acylation reaction is carried out, to give the compound (VIIIa), by reacting the compound (XIIa) or its salt with a base with an acylating agent (VIIa) or its functional derivative at the carboxy group such as its acid halide (e.g. acid chloride), acid anhydride, amide, azide and ester (e.g. ethyl ester, cyanomethyl ester, p-nitrophenyl ester, pentachlorophenyl ester, 2,4,5-trichlorophenyl ester, propargyl ester, carboxymethyl thioester, pyranyl ester, methoxymethyl ester, phenyl thioester, N-hydroxysuccinimide), usually in a solvent (e.g. ether, acetone, dioxane, acetonitrile, chloroform, ethylene chloride, tetrahydrofuran, ethyl acetate, pyridine) under cooling, at room temperature or under heating, whereby the hydroxy group is converted into the acyloxy group. When used the compound (VIIa) in a free carboxy group in the acylation, there may be used a condensing agent such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonyldiimidazole, N,N-carbonyldipyrazole, N,N'-carbonyldi(2-methylimidazole), pentamethyleneketene-N-cyclohexylimine, diphenylketene-N-cyclohexylimine, alkoxyacetylene, 1-alkoxy-1-chloroethylene, 2-ethyl-7-hydroxybenzisoxazolium salt, 2-ethyl-5-(m-sulfophenyl)isoxazolium hydroxide or the like. There may be also added a base such as alkali metal carbonate, trialkylamine or pyridine.

The objective compound (Ia) as obtained according to the above-mentioned procedures can be converted to its salt by a conventional method.

Thus obtained compound (Ia) and its salt are useful an intermediate for the production of Cephalosporin derivatives which are valuable as antibiotics, for example, represented by the formula:

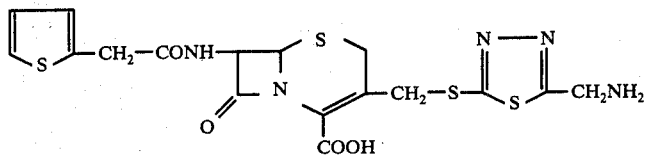

which can be prepared by reacting 7-(2-thienylacetamido) cephalosporanic acid with 5-aminomethyl-1,3,4-thiadiazole-2-thiol provided by this invention according to a conventional procedure.

The invention will be more fully illustrated in the examples which follow. These example are given by way of illustration and are not be considered as limiting.

EXAMPLE 1

7-(2-Thienyl)acetamido cephalosporanic acid (2.03 g.), 5-aminomethyl-1,3,4-thiadiazole-2-thiol hydrochloride (0.93 g.) and sodium bicarbonate (1.26 g.) were dissolved in pH5.2 phosphate buffer (100 ml.), and the solution was stirred at 60° – 65° C for 7 hrs. After the reaction, the precipitating crystals were collected by filtration to give 7-(2-thienyl)acetamido-3-(5-aminomethyl-1,3,4-thiadiazol-2-yl)thiomethyl-3-cephem-4-carboxylic acid (1.3 g.). m.p. 198°–202° C (dec.).

N.M.R. (D$_2$O+NaHCO$_3$)ppm:3.28(1H,d,J=18Hz), δ 3.72(1H,d,J=18Hz), 3.87(2H,s), 4.0 – 4.45 (2H, broad s), 4.56 (2H,s), 5.01(1H,d,J=5Hz), 5.58(1H,d,J32 5Hz), 6.88 – 7.40(3H,m).

EXAMPLE 2

7-(1H-Tetrazol-1-yl)acetamidocephalosporanic acid (3.82 g.), 5-acetamidomethyl-1,3,4-thiadiazole-2-thiol (1.89 g.) and sodium bicarbonate (1.68 g.) were dissolved in pH6.4 phosphate buffer (100 ml.), and the solution was stirred at 60°–65° C for 5 hrs. The reaction mixture was washed with ethyl acetate and the aqueous layer was separated out. The aqueous solution was adjusted to pH3 with 5% hydrochloric acid, and then washed with ethyl acetate (150 ml.). To the aqueous solution was added ethyl acetate and the resultant mixture was stirred. The precipitating crystals were collected by filtration to give 7-(1H-tetrazol-1-yl)acetamido-3-(5-acetamidomethyl-1,3,4-thiadiazol-2-yl)thiomethyl-3-cephem-4-carboxylic acid (1.8 g.). m.p. 141°–144° C (dec.). The above ethyl acetate washings and the mother liquid were put together and then concentrated under reduced pressure to the volum of about 30 ml. The precipitating crystals were collected to give also the objective compound (0.4 g.). Total yield was 2.2 g.

I.R.: $\nu_{max}^{Nujol}$ cm$^{-1}$: 3500, 3275, 1765, 1725, 1670

N.M.R.: δ(DMSO-d$_6$)ppm:1.92(3H,s), 3.73(2H, broad s), 4.15 – 4.73(2H,m), 4.59(2H,d,J=6Hz), 5.15(1H,d,J=4.5Hz), 5.42(2H,s), 5.69(d,J=4.5Hz). 5.83(d,J=5Hz)1H, 6.10(1H,m), 8.50 – 8.65(1H,m), 9.18(1H,s), 9.35(1H,d,J=7Hz)

EXAMPLE 3

7-(2-Thienyl)acetamidocephalosporanic acid (3.2 g.), 5-acetamidomethyl-1,3,4-thiadiazole-2-thiol (1.42 g.) and sodium bicarbonate (1.26 g.) were dissolved in pH6.4 phosphate buffer (75 ml.) and the solution was stirred at 60°–65° C for 4.5 hrs. The reaction mixture was washed with ethyl acetate, and the aqueous layer was separated out. The aqueous solution was adjusted to pH2 with 5% hydrochloric acid and then extracted with ethyl acetate. The extract was washed with a saturated aqueous solution of sodium chloride, and dried over magnesium sulfate, and then the solvent was evaporated. The residue was washed with ether to give 7-(2-thienyl)acetamido-3-(5-acetamidomethyl-1,3,4-thiadiazol-2-yl)thiomethyl-3-cephem-4-carboxylic acid (2.15 g.) m.p. 146°–151° C (dec.).

I.R.: $\nu_{max}^{Nujol}$ cm$^{-1}$: 3250, 1760, 1700, 1650

N.M.R.: δ(DMSO-d$_6$)ppm:2.89(3H,s), 3.70(2H, broad s), 3.78(2H,s), 4.21(1H,d,J=14Hz), 4.58(1H,d,J=14Hz), 4.59(2H,d,J=6Hz), 5.09(1H,d,J=5Hz), 5.63(d,J=5Hz). 5.77(d,J=5Hz)1H, 6.88 – 742 (3H,m), 8.60 – 9.00(2H,m).

EXAMPLE 4

7-(1H-Tetrazol-1-yl)acetamidocephalosporanic acid (1.9 g.), 5-tert-butoxycarbonylaminomethyl-1,3,4-thiadiazole-2-thiol (1.24 g.) and sodium bicarbonate (840 mg.) were added to pH6.4 phsophate buffer (50 ml.) and the mixture was stirred at 60°–65° C for 4 hrs. The reaction mixture was washed with ether (50 ml.) four times and the aqueous layer was separated out. The aqueous solution was adjusted to pH2 with 5% hydrochloric acid and then extracted with ethyl acetate (70 ml.) three times. The extract was washed with a saturated aqueous solution of sodium chloride and dried over magnesium sulfate, and then the solvent was evaporated under reduced pressure. The residue was washed with ether to give 7-(1H-tetrazol-1-yl)acetamido-3-(5-tertbutoxycarbonylaminomethyl-1,3,4-thiadiazol-2-yl)thiomethyl-3-cephem-4-carboxylic acid (1.48 g.). m.p. 192°–196° C (dec.).

N.M.R.: δ(DMSO-$d_6$)ppm:1.38(9H,s), 3.75(2H, broad s), 4.28(1H,d,J=18Hz), 4.64(1H,d,J=18Hz), 4.49(2H,d,J=6Hz), 5.17(1H,d,J=5Hz), 5.42(2H,s), 5.69(d,J=5Hz). 5.82(d,J=5Hz)1H, 7.55 – 7.90(1H,m), 9.23(1H,s), 9.35(1H,d,J=8Hz)

7-(1H-Tetrazol-1-yl)acetamido-3-(5-tert-butoxycarbonylaminomethyl-1,3,4-thiadiazol-2-yl)-thiomethyl-3-cephem-4-carboxylic acid (300 mg.) obtained above was dissolved in formic acid (1.5 ml.) and the solution was stirred at room temperature for 4.5 hrs. The formic acid was distilled off under reduced pressure from the reaction mixture, and ethyl acetate was added to the residue to give brown powder (245 mg.). The powder was dissolved in a mixture of water (1 ml.) and dimethylformamide (1 ml.), and to the solution was added ethanol (6 ml.) to give pale yellow powder of 7-(1H-tetrazol-1-yl)acetamido-3-(5-aminomethyl-1,3,4-thiadiazol-2-yl)thiomethyl-3-cephem-4-carboxylic acid (140 mg.). The product was identified with the one obtained in Example 6 by thin-layer chromatography.

EXAMPLE 5

7-Phenylacetamidocephalosporanic acid (3.9 g.), 5-aminomethyl-1,3,4-thiadiazole-2-thiol (2.40 g.) and sodium bicarbonate (1.93 g.) were added to pH6.4 phosphate buffer (85 ml.), and the solution was stirred at 60° C for 5 hrs. The precipitating crystals in the reaction mixture were collected by filtration and washed with ethanol and ether to give 7-phenylacetamido-3-(5-aminomethyl-1,3,4-thiodiazol-2-yl)thiomethyl-3-cephem-4-carboxylic acid (3.3 g.) m.p. 208°–210° C (dec.)

I.R.: $\nu_{max}^{Nujol}$ cm$^{-1}$: 3250, 1760, 1663

N.M.R.: δ($D_2O$+NaHCO$_3$)ppm:3.24(1H,d,J=18Hz), 3.67(1H,d,J=18Hz), 3.68(2H, broad s), 4.02(1H,d,J=14Hz), 4.51(1H,d,J=14Hz), 4.63(2H,s), 5.03(1H,d,J=4Hz), 5.67(1H,d,J=4Hz), 7.3(5H,s)

U.V.: $\lambda_{max}^{pH6.4\ phosphate\ buffer}$ mμ:274, E%=248

Analysis for $C_{19}H_{19}N_5O_3S_3$:Calculated C,47.78;H,4.01;N,14.67;S,20.14. Found C,47.38;H,3.85;N,14.00;S,20.36.

EXAMPLE 6

7-(1H-Tetrazol-1-yl)acetamidocephalosporanic acid (3.82 g.), 5-aminomethyl-1,3,4-thiadiazole-2-thiol hydrochloride (1.85 g.) and sodium bicarbonate (2.52 g.) were added to pH5.2 phosphate buffer (150 ml.), and the solution was adjusted to pH5.0–5.2 with 10% hydrochloric acid. After the solution was stirred at 60° C for 8 hrs., methyl isobutyl ketone (70 ml.) was added to the solution, and the mixture was stirred at 60° C for 30 minutes. The methyl isobutyl ketone layer was removed, and the aqueous layer was allowed to stand in an ice box. The precipitating crystals were collected by filtration to give 7-(1H-tetrazol-1-yl)acetamido-3-(5-aminomethyl-1,3,4-thiadiazol-2-yl)thiomethyl-3-cephem-4-carboxylic acid (1.91 g.). m.p. 193°–198° C (dec.). To the mother liquid was added ethanol (50 ml.), and the solution was allowed to stand in an ice box. The precipitating crystals were collected by filtration to give also the objective compound (1.30 g.). Total yield was 3.21 g.

I.R.: $\nu_{max}^{Nujol}$ cm$^{-1}$: 3280, 1755, 1675

N.M.R.: δ($D_2O$+NaHCO$_3$)ppm:3.41(1H,d,J=18Hz), 3.85(1H,d, J=18Hz), 4.03(1H,d,J=14Hz), 4.50(1H,d,J=14Hz), 4.59(2H,s), 5.13(1H,d,J=5Hz), 5.58(2H,s), 5.69(1H,d,J=5Hz), 9.35(1H,s),

EXAMPLE 7

7-(1H-Tetrazol-1-yl)acetamidocephalosporanic acid (2.86 g.), 5-(2-aminoethyl)-1,3,4-thiadiazole-2-thiol hydrochloride (1.49 g.) and sodium bicarbonate (1.89g.) were dissolved in pH5.2 phosphate buffer (100 ml.), and the solution was stirred at 60°–65° C for 8 hrs. The reaction mixture was cooled to the room temperature, and then adsorbed on Amberlite XAD-4 (200 ml.) in a column. The column was washed with water (2.7 l.) and then eluted with methanol (2 l.). The methanol was evaporated from the eluate under reduced pressure to give 7-(1H-tetrazol-1-yl)acetamido-3-[5-(2-aminoethyl)-1,3,4-thiadiazol-2-yl]thiomethyl-3-cephem-4-carboxylic acid (1.7 g.). The product was purified by washing with aqueous methanol, m.p. 187°–191° C (dec.).

I.R.: $\nu_{max}^{Nujol}$ cm$^{-1}$: 1760, 1690, 1580

N.M.R.: δ($D_2O$+NaHCO$_3$)ppm:3.2 – 3.8(6H,m), 4.08(1H,d, J=13.5Hz), 4.52(1H,d,J=13.5Hz), 5.17(1H,d, J=4.5Hz), 5.59(2H,s), 5.70(1H,d,J=4.5Hz), 9.38(1H,s)

EXAMPLE 8

7-(2-Thienyl)acetamidocephalosporanic acid (2.03 g.), 5-(2-aminoethyl)-1,3,4-thiadiazole-2-thiol hydrochloride (1 g.) and sodium bicarbonate (1.26 g.) were added to pH5.2 phosphate buffer (100 ml.), and the solution was adjusted to pH5.2 with 5% hydrochloric acid and then stirred at 60° C for 9 hrs. The reaction mixture was allowed to stand overnight in a refrigerator. The oily layer was separated, washed with water, and then powdered by adding a mixture of ethyl acetate and acetonitrile to give crude 7-(2-thienyl)acetamido-3-[5-(2-aminoethyl)-1,3,4-thiadiazol-2-yl]thiomethyl-3-cephem-4-carboxylic acid (0.50 g.). The aqueous solution after removing the oily layer was concentrated under reduced pressure to the volume of about 20 ml. The precipitating oily substance was treated in the same way as above to give also the crude objective compound (1.00 g.). The crude objective compound (1.5 g.) was suspended in methanol (100 ml.), and water (3 ml.) was added to the suspension. The aqueous suspension was stirred at room temperature for 4 hrs. To give the purified product (1.1 g.). m.p. 177°–179° C (dec.).

I.R.: $\nu_{max}^{Nujol}$ cm$^{-1}$: 1750, 1650, 1610,

N.M.R.: δ(DMSO-$d_6$)ppm:3.1 – 3.7 (6H,m), 3.76(2H,s), 4.05(1H,d,J=14Hz), 4.68(1H,d,J=14Hz), 5.02(1H,d,J=4.5Hz), 5.10–5.75(3H,m), 6.85–7.40(3H), 9.03(1H,d,J=8Hz)

EXAMPLE 9

7-Aminocephalosporanic acid (1.36 g.), 5-acetamidomethyl-1,3,4-thiadiazole-2-thiol(1.04 g.) and sodium bicarbonate (885 mg.) were dissolved in water (70 ml.), and the solution was stirred at 60° C for 5 hrs. After the reaction, the reaction mixture was adjusted to pH5, and then allowed to stand overnight in a refrigerator. The precipitating crystals were collected by filtration to give 7-amino-3-(5-acetamidomethyl-1,3,4-thiadiazol-2yl)thiomethyl-3-cephem-4-carboxylic acid (1.03 g.) m.p. 195°–197° C (dec.).

I.R.: $\nu_{max}^{Nujol}$ cm$^{-1}$: 1795, 1640

N.M.R.: δ(D$_2$O+DCl)ppm:2.12(3H,s), 3.83(2H,s), 4.30(1H,d,J=14Hz), 4.64(1H,d,J=14Hz), 4.79(2H,s), 5.22(1H,d,J=4.5Hz), 5.37(1H,d,J=4.5Hz)

EXAMPLE 10

7-Methylthioacetamidocephalosporanic acid (1.44 g.), 5-aminomethyl-1,3,4-thiadiazole-2-thiol hydrochloride (740 mg.) and sodium bicarbonate (1.02 g.) were dissolved in pH5.2 phosphate buffer (40 ml.). The solution was adjusted to pH4.5 with 10% hydrochloric acid, and stirred at 60°–65° C for 7 hrs. The precipitate in the reaction mixture was separated out by filtration, washed with water, and then washed with acetone to give 7-methylthioacetamido-3-(5-aminomethyl-1,3,4-thiadiazol-2-yl)-thiomethyl-3-cephem-4-carboxylic acid (1.13 g.). m.p. 201°–205° C (dec.)

I.R.: $\nu_{max}^{Nujol}$ cm$^{-1}$: 1790, 1625
N.M.R.: δ(D$_2$O+NaHCO$_3$)ppm:2.18(3H,s), 3.34(2H,s), 3.44(1H,d,J=18Hz), 3.87(1H,d,J=18Hz), 4.05(1H,d,J=14Hz), 4.55(1H,d,J=14Hz), 4.62(2H,s), 5.17(1H,d,J=4.5Hz), 5.67(1H,d,J=4.5Hz)

EXAMPLE 11

5-Tert-butoxycarbonylaminomethyl-1,3,4-thiadiazole-2-thiol(1.24 g.) was dissolved in acetone (10 ml.). The solution was added to the aqueous solution (40 ml.) containing sodium bicarbonate (0.84 g.). The mixed solution was warmed on water bath heating at 70°–75° C. To the solution was added all at once 7-aminocephalosporanic acid (1.35 g.) at 55° C. The mixture was stirred at 65°–70° C for 2 hrs. and then cooled to 0°–5° C with ice. The reaction mixture was adjusted to pH5.0–5.2 with 10% hydrochloric acid. The precipitating pale yellow substance was separated out by filtration, washed with water and acetone, and then dried to give 7-amino-3-(5-tert-butoxycarbonylaminomethyl-1,3,4-thiadiazol-2-yl)thiomethyl-3-cephem-4-carboxylic acid (1.28 g.) m.p. over than 220° C.

I.R.: $\nu_{max}^{Nujol}$ cm$^{-1}$: 1805, 1700, 1625
N.M.R.: δ (D$_2$O+NaHCO$_3$)ppm:1.41(9H,s), 3.39(1H,d,J=17Hz), 3.79(1H,d,J=17Hz), 4.08(1H,d,J=14Hz), 4.55(1H,d,J=14Hz), 4.60(2H,s), 5.08(1H,d,J=4.5Hz), 5.50(1H,d,J=4.5Hz)

EXAMPLE 12

Sodium 7-(1H-tetrazol-1-yl)acetamidocephalosporanate (2.02 g.), 1-(2-aminoethyl)-1-H-tetrazole-5-thiol (0.90 g.) and sodium bicarbonate (0.84 g.) were dissolved in water (50 ml.). The solution was adjusted to pH 3.4–3.6 and stirred at 60°–65° C for 5.5 hrs. The reaction mixture was lyophilized and the residue was dissolved in water (10 ml.) and then adsorbed on Amberlite XAD-2 (100 ml.). The column was washed with water and then eluted with ethanol containing 20% of water. The solvent was evaporated from the eluate under reduced pressure to give 7-(1H-tetrazol-1-yl)acetamido-3-[1-(2-aminoethyl)-1H-tetrazol-5-yl]thiomethyl-3-cephem-4carboxylic acid (0.60 g.). m.p. 173°–176° C (dec.).

I.R.: $\nu_{max}^{Nujol}$ cm$^{-1}$: 1767, 1690, 1590, (broad)
N.M.R.: δ (D$_2$O+NaHCO$_3$)ppm:3.45–3.75 (4H,m), 4.22, 4.43(2H,AB-q, J=14Hz), 4.5–4.7 (2H,m), 5.16(1H,d,J=5Hz), 5.61(2H,s), 5.70(1H,d,J=5Hz), 7.70(1H,s)

EXAMPLE 13

7-(2-Thienyl)acetamidocephalosporanic acid (3.94 g.), 1-[2-tert-butoxycarbonylaminoethyl]-1H-tetrazole-5-thiol (2.45 g.) and sodium bicarbonate (1.68 g.) were dissolved in water (100 ml.), and the solubtion was stirred at 60°–63° C for 7 hrs. The reaction mixture was washed with ether (50 ml.) twice, adjusted to pH 1–2 with 10% hydrochloric acid, and then extracted with ethyl acetate (150 ml.) under ice-cooling. The remaining aqueous layer was washed with ethyl acetate (100 ml.) twice. The ethyl acetate extract and washing were put together, washed with saline and then dried over magnesium sulfate. The ethyl acetate was evaporated under reduced pressure to give yellow powder (5.28 g.). The powder was purified by silica gel column chromatography to give 7-(2-thienyl)acetamido-3-[1-(2-tert-butoxycarbonylaminoethyl)-1H-tetrazol-5-yl]thiomethyl-3-cephem-4-carbonxylic acid (3.18 g.) m.p. 88°–93° C (dec.).

I.R.: $\nu_{max}^{Nujol}$ cm$^{-1}$: 3300, 1700 (broad)
N.M.R.: δ(DMSO-d$_6$+D$_2$O)ppm:1.35(9H,s), 3.35 (2H, broad s), 3.6–3.85(4H,m,) 4.15–4.50(4H,m), 5.03(1H,d,J=5Hz), 5.64(1H,d,J=5Hz), 6.80–7.40(3H,m)

7-(2-Thienyl)acetamido-3-[1-(2-tert-butoxycarbonylaminoethyl)-1H-tetrazol-5-yl]thiomethyl-3-cephem-4carboxylic acid (2.70 g.) obtained above was dissolved in formic acid (15 ml.). The solution was stirred at room temperature for 3 hrs. The formic acid was evaporated under reduced pressure and the residue was treated with acetonitrile to give a powder. The powder was washed with acetonitrile and ether respectively and then dried to give 7-(2-thienyl)acetamido-3-[1-(2-aminoethyl)1H-tetrazol-5-yl]thiomethyl-3-cephem-4-carboxylic acid (1.86 g.), m.p. 158°–162° C (dec.).

I.R.: $\nu_{max}^{Nujol}$ cm$^{-1}$: 3250, 1760, 1655, 1625, 1570
N.M.R.: δ(D$_2$O+NaHCO$_3$)ppm:3.35–3.65(4H,m), 3.83(2H,s), 4.10–4.60(4H,m), 5.05(1H,d,J=4.5Hz), 5.58(1H,d,J=4.5Hz), 6.90–7.40(3H,m)

EXAMPLE 14

7-Amino-3-(5-tert-butoxycarbonylaminomethyl-1,3,4-thiadiazol-2-yl)thiomethyl-3-cephem-4-carboxylic acid (4.59 g.) and sodium bicarbonate (2.52 g.) were added to a mixture of water (50 ml.) and acetone (40 ml.), and the resultant mixture was stirred at room temperature for 10 minutes. To the mixture was added acetone solution (10 ml.) including 4-methyl-1,2,5-oxadiazole-3-acetylchloride (1.926 g.) at 0°–3° C for 20 minutes, and the mixture was stirred at the same temperature for an hour and then at room temperature for 1.5 hrs. Acetone was distilled off under reduced pressure from the reaction mixture, and to the residue was added ethyl acetate (150 ml.). The solution was adjusted to pH2 by adding 10% hydrochloric acid under ice-cooling water stirring, and the insoluble substance was filtered off. The ethyl acetate layer was separated out, and the remaining aqueous layer was extracted with ethyl acetate (50 ml.). The ethyl acetate solutions were put together, and washed with a saturated aqueous solution of sodium chloride, and then dried over magnesium sulfate. The solvent was evaporated under reduced pressure, and to the residue was added hot acetone (10 ml.). The insoluble substance was filtered off. The filtrate was purified by silica-gel column chromatography [eluent: ethyl acetate (50 parts) + acetic acid (1 part)]. The obtained product was added to methanol (10 ml.), and the solution was stirred for an hour. The insoluble substance was obtained by filtration, washed with methanol and then with ether to give 7-(4-methyl-1,2,5- oxadiazol-3-yl)-acetamido-3-(5-tert-butoxycarbonylaminomethyl-1,3,4-thiadiazol-2-yl)thiomethyl-3-cephem-4-carboxylic acid (1.65 g.). m.p. 154.5°–156° C (dec.).

I.R.: $\nu_{max}^{Nujol}$ cm$^{-1}$: 3340, 1775, 1710 (sholder), 1690, 1660

N.M.R.: δ(DMSO-d$_6$)ppm: 1.4(9H,s), 2.34(3H,s) 3.72(2H, broad s), 3.92(2H,s) 4.23, 4.60(2H,AB-q,J=14Hz), 4.48(2H,d,J=6Hz), 5.13(1H,d,J=4.5Hz), 5.69(1H,d,d,J=4.5Hz, 7.5Hz), 7.67(1H, broad s), 9.38(1H,d,J=7.5Hz)

7-(4-Methyl-1,2,5-oxadiazol-3-yl)acetamido-3-(5-tert-butoxycarbonylaminomethyl-1,3,4-thiadiazol2-yl)thiomethyl-3-cephem-4-carboxylic acid (1.5 g.) obtained above was added to 98–100% formic acid (8 ml.), and the solution was stirred at room temperature for 3 hrs. The formic acid was distilled off under reduced pressure from the reaction mixture. The residue was powdered by treating ethyl acetate. The precipitate was obtained by filtration, and washed with ethyl acetate and then with ether to give 7-(4-methyl-1,2,5-oxadiazol-3-yl)-acetamido-3-(5-aminomethyl-1,3,4-thiadizol-2-yl)-thiomethyl-3-cephem-4-carboxylic acid (1.272 g.). This product was added to acetonitrile (26 ml.). Water (1.3 ml.) was added to the solution by dropwise at room temperature under stirring, and the mixture was stirred at room temperature for 2 hrs. The crystals were collected by filtration with suction, and washed with acetonitrile and then with ether. The crystals were added to methanol (10 ml.) and the mixture was stirred at room temperature for an hour. The crystals were collected by filtration, and washed with methanol and then with ether to give the purified product (1.106 g.). m.p. 171°–173° C (dec.).

I.R.: $\nu_{max}^{Nujol}$ cm$^{-1}$: 3250, 1760, 1660

N.M.R.: δ(D$_2$O+NaHCO$_3$)ppm: 2.40(3H,s), 3.42, 3.84(2H,AB-q,J=17.5Hz), 4.03(2H,s), 4.07, 4.54(2H,AB-q,J=14Hz), 4.60(2H,s), 5.14(1H,d,J=4.5Hz), 5.66(1H,d,J=4.5Hz)

EXAMPLE 15

A mixture of dimethylformamide (0.85 g.) and thionyl chloride (1.95 g.) was heated at 40°–50° C for 30 minutes, and the excess of thionyl chloride was distilled off under reduced pressure. The residue was suspended in methylene chloride (20 ml.). To the suspension was added D-mandelic acid (0.84 g.) at −5° − −10° C all at once. After stirring the mixture at the same temperature for 15 minutes, methylene chloride solution (3 ml.) containing triethylamine (1.11 g.) was added dropwise to the mixture at −50° − −60° C for 10 minutes. The mixture was stirred at the same temperature for 30 minutes. To the solution was added a solution of 7-amino-3-(5-tert-butoxycarbonylaminomethyl1,3,4-thiadiazol-2-yl)thiomethyl-3-cephem-4-carboxylic acid (2.30 g.), N,O-bis(trimethylsilyl)acetamide (2.0 g.) and methylene chloride (20 ml.) at −50° − −60° C all at once. The mixture was stirred at the same temperature for 4 hrs. and then at room temperature for an hour. Methylene chloride was distilled off under reduced pressure from the reaction mixture. The residue was dissolved in a mixture of ethyl acetate (150 ml.), acetone (50 ml.) and 5% hydrochloric acid (50 ml.). The aqueous layer was separated out and extracted with ethyl acetate (100 ml.) twice. The extracts and the ethyl acetate layer obtained above were put together, and it was washed with water and then dried over magnesium sulfate. The solvent was evaporated under reduced pressure to give powder. The powder and sodium bicarbonate (3 g.) were dissolved in a mixture of water (50 ml.) and acetone (20 ml.), and the solution was stirred at room temperature for 2 hrs., and then acetone was evaporated. Thus obtained aqueous layer was washed with ether, adjusted to pH1, and extracted with ethyl acetate. The extract was washed with water and dried over magnesium sulfate, and the ethyl acetate was evaporated under reduced pressure. The residue was purified by silica-gel column chromatography to give 7-(D-mandelamido)-3-(5-tert-butoxycarbonylaminomethyl-1,3,4-thiadiazol-2-yl)thiomethyl-3-cephem-4-carboxylic acid (1.32 g.). m.p. 115° − 121° C (dec.)

I.R.: $\nu_{max}^{Nujol}$ cm$^{-1}$: 3350, 1780, 1710 (sholder), 1690

N.M.R.: δ(DMSO-d$_6$+D$_2$O)ppm: 1.39(9H,s), 3.62(2H, broad s), 4.28, 4,51(2H,AB-q,J=14Hz), 4,49(2H,s), 5.04(1H,d,J=5Hz), 5.13(1H,s), 5.65(1H,d,J=5Hz), 7.20–7.50(5H,m)

7-(D-mandelamido)-3-(5-tert-butoxycarbonyl-aminomethyl-1,3,4-thiadiazol-2-yl)thiomethyl-3-cephem-4-carboxylic acid (800 mg.) obtained above was dissolved in formic acid (4 ml.), and the solution was stirred at room temperature for 2 hrs. The formic acid was distilled off under reduced pressure from the reaction mixture, and the residue was powdered by treating with acetonitrile. The precipitate was obtained by filtration and washed with acetonitrile and then with ether to give 7-(D-mandelamido)-3-(5-aminomethyl-1,3,4-thiadiazol-2-yl)thiomethyl-3-cephem-4-carboxylic acid (620 mg.). m.p. 168°–173° C (dec.)

I.R.: $\nu_{max}^{Nujol}$ cm$^{-1}$: 3300 (broad), 1765, 1670, 1600 (broad)

N.M.R.: δ(D$_2$O+NaHCO$_3$)ppm: 3.18(1H,d, J=18Hz), 3.65(1H,d,J=18Hz), 4.00(1H,d,J=14Hz), 4,49(1H,d,J=14Hz), 4.58(2H,s), 5.01 (1H,d,J=5Hz), 5.33(1H,s), 5.64(1H,d,J=5Hz), 7.20–7.60(5H,m)

EXAMPLE 16

A mixture of dimethylformamide (2.42 g.) and thionyl chloride (5.85 g.) was heated at 40°–50° C for 30 minutes. The excess of thionyl chloride was distilled off under reduced pressure, and the residue was suspended in methylene chloride (60 ml.). To the suspension was added 2-thienyl-DL-glycolic acid (2.61 g.) all at once at −5° − −10° C, and the mixture was stirred at the same temperature for 15 minutes. Methylene chloride solution (10 ml.) of triethylamine (3.33 g.) was added dropwise to the above mixture at −50° − −60° C for 10 minutes, and the mixture was stirred at the same temperature for 30 minutes. To the mixture was added all at once a solution of 7-amino-3-(5-tert-butoxycarbonylaminomethyl-1,3,4-thiadiazol-2-yl)thiomethyl-3-cephem-4-carboxylic acid (6.9 g.), N,O-bis(trimethylsilyl)acetamide (6.1 g.) and methylene chloride (60 ml.) at −50° − −60° C. The mixture was stirred at the same temperature for 4 hrs. and then at room temperature for an hour. The methylene chloride was distilled off from the reaction mixture. The residue was dissolved in a mixture of acetone (50 ml.) and water (30 ml.), and the solution was poured into ethyl acetate (300 ml.). The organic solvent layer was separated out, washed with 5% hydrochloric acid and water respectively, and dried over magnesium sulfate. The solution was treated with activated charcoal powder, and the solvent was evaporated under reduced pressure to give a powder (7.36 g.). The powder and sodium bicarbonate were dissolved in a mixture of acetone (50 ml.) and water (150 ml.). The solution was stirred at room temperature for 4 hrs. Ethyl acetate (400 ml.) was added to the solution, and the mixture was adjusted to pH1 with 10% hydrochloride acid under cooling. The aqueous layer was separated out, and extracted with ethyl acetate (150 ml.) twice. The extract and the ethyl acetate layer obtained above were put together, and it was washed with water and then dried over magnesium sulfate.

The solvent was evaporated, and the residue was purified by silica-gel column chromatography to give 7-(2-thiehyl-DL-glycolamido)-3-(5-tert-butoxycarbonylaminomethyl-1,3,4-thiadiazol-2-yl)thiomethyl-3-cephem-4-carboxylic acid (1.50 g.). m.p. 119°–125° C (dec.).

I.R.: $v_{max}^{Nujol}$ cm$^{-1}$: 3350, 1780, 1710 (sholder), 1690
N.M.R.: $\delta$(DMSO-d$_6$+D$_2$O)ppm: 1.40(9H,s), 3.59(2H, broad s), 4.20, 4.47(2H,AB-q,J=14Hz), 5.01(1H,d,J=5Hz), 5.24(½H,s), 5.28(½H,s), 5.56(1H,d,J=5Hz), 6.80–7.35(3H,m)

7-(2-Thienyl-DL-glycolamido)-3-(5-tert-butoxycarbonylaminomethyl-1,3,4-thiadiazol-2-yl)thiomethyl3-cephem-4-carboxylic acid (1.35 g.) obtained above was dissolved in formic acid (8 ml.), and the solution was stirred at room temperature for 2 hrs. Formic acid was distilled off under reduced pressure from the reaction mixture. The residue was added in acetonitrile, and the mixture was stirred at room temperature for an hour. The precipitate was obtained by filtration, washed with acetonitrile and ether respectively and then dried to give 7-(2-thienyl-DL-glycolamido)-3-(5-aminomethyl-1,3,4-thiadiazol-2-yl)thiomethyl-3-cephem4-carboxylic acid (1.14 g.) m.p. 173°–175° C (dec.).

I.R.: $v_{max}^{Nujol}$ cm$^{-1}$: 3300 (broad), 1768, 1675, 1600 (broad)
N.M.R.: $\delta$(D$_2$O+NaHCO$_3$)ppm: 3.35–3.80(2H,m), 3.90–4.60(2H,m), 4.63(2H,s), 5.05(1H,d,J=5Hz), 5.70(1H,s), 5.73(1H,d,J=5Hz), 6.90–7.50 (3H,m)

EXAMPLE 17

Dried acetone solution (5 ml.) of pivalyl chloride (1.45 g.) was added dropwise to a solution of 3-(2-thienyl)-3-(tert-butoxycarbonylamino-DL-propionic acid (3.25 g.), triethylamine (1.21 g.) and dried acetone (60 ml.) at −10° – −15° C for 20 minutes, and the mixture was stirred at the same temperature for an hour. On the other hand, 7-amino-3-(5-tert-butoxycarbonylaminomethyl-1,3,4-thiadiazol-2yl)thiomethyl-3-cephem-4-carboxylic acid (4.5 g.) and triethylamine (3.03 g.) were dissolved in a mixture of water (15 ml.) and acetone (60 ml.), and it was added at once to the solution obtained above at −50° – −60° C. The mixture was stirred at the same temperature for 1.5 hrs. and then at room temperature for 2 hrs. To the reaction mixture was added water (50 ml.), and acetone was evaporated. Ethyl acetate was added to the remaining aqueous layer, and it was adjusted to pH1 with 10% hydrochloric acid. The insoluble substance was filtered off, and the aqueous layer was separated out and extracted with ethyl acetate (100 ml.) twice. The extract and the ethyl acetate layer obtained above were put together, and it was washed with 5% hydrochloric acid and water respectively and then dried over magnesium sulfate. Ethyl acetate was distilled off under reduced pressure from the solution, and the residue was washed with ether to give 7-[3-(2-thienyl)-3-tert-butoxycarbonylamino-DL-propionamido]-3-(5-tert-butoxycarbonylaminomethyl-1,3,4-thiodiazol-2-yl)thiomethyl-3-cephem-4-carboxylic acid (4.96 g.) m.p. 145°–149° C (dec.).

I.R.: $v_{max}^{Nujol}$ cm$^{-1}$: 3350, 1780, 1710 (sholder), 1690, 1660 (sholder)
N.M.R.: $\delta$ (DMSO-d$_6$+D$_2$O)ppm: 1.38(18H,s), 2.60–2.90 (2H,m), 3.60(2H, broad s), 4.30–4.55 (2H,m), 4.50(2H,s), 4.90–5.30(2H,m), 5.50–5.70(1H,m), 6.45–6.85(3H,m)

7-[3-(2-Thienyl)-3-tert-butoxycarbonylamino-DL-propionamido]-3-(5-tert-butoxycarbonylaminomethyl-1,3,4-thiadiazol-2-yl)thiomethyl-3-cephem-4-carboxylic acid (2.0 g.) obtained above was dissolved in formic acid (15 ml.), and the solution was stirred at room temperature for 3.5 hrs. Formic acid was distilled off under reduced pressure from the reaction mixture, and the residue was powdered by treating with acetonitrile. The precipitate was obtained by filtration and suspended in a mixture of acetonitrile (70 ml.) and water (1.4 ml.). The suspension was stirred for 2 hrs. and filtered to give 7-[3-(2-thienyl)-3-amino-DL-propionamido]-3-(5-aminomethyl-1,3,4-thiadiazol-2-yl)thiomethyl-3-cephem-4-carboxylic acid (1.2 g.) m.p. 183°–187° C (dec.).

I.R.: $v_{max}^{Nujol}$ cm$^{-1}$: 1770, 1660, 1580 (broad)
N.M.R.: $\delta$ (D$_2$O+DCl)ppm: 3.34(2H,s, J=8Hz), 3.72(2H, broad s), 4.40(2H, broad s), 4.78(2H,s), 5.15(1H,d, J=5Hz), 5.22(1H,t, J=8Hz), 5.55(½H,d, J=5Hz), 5.62(1−2H,d, J=5Hz), 7.00–7.65(3H,m)

EXAMPLE 18

7-(2-Thienyl)acetamido cephalosporanic acid (2.44 g.), 5-(2-hydroxyethyl)-1,3,4-thiadiazole 2-thiol (0.97 g.) and sodium bicarbonate (1.01 g.) were dissolved in pH 6.4 phosphate buffer (60 ml.), and the solution was stirred at 60°–65° C for 7 hrs. After the reaction was over, the reaction mixture was washed with ethyl acetate (30 ml.) three times. The aqueous layer was separated out, adjusted to pH2 with 10% hydrochloric acid, and then extracted with ethyl acetate. The extract was washed with a saturated aqueous solutions of sodium chloride and dried over magnesium sulfate, and then the solvent was evaporated under reduced pressure. The residue was powdered with ether to give 7-(2-thienyl)acetamido-3-[5-(2-hydroxyethyl)1,3,4-thiadiazol-2-yl]thiomethyl-3-cephem-4-carboxylic acid (2.03 g.). mp. 84°–88° C (dec.).

I.R.: $v_{max}^{Nujol}$ cm$^{-1}$: 1770, 1710, 1660
N.M.R.: $\delta$ (DMSO-d6)ppm: 3.17 (2H,t,J=5Hz), 3.55–4.05(6H,m) 4.20(1H,d, J=13.5Hz), 4.58(1H,d, J=13.5Hz), 5.10(1H,d, J=5Hz), 5.69(1H,d,d, J=5Hz, 8Hz), 6.88–7.05(2H,m), 7.28–7.43(1H,m), 9.12 (1H,d,J=8Hz)

EXAMPLE 19

7-(1H-Tetrazol-1yl)acetamido cephalosporanic acid (2.29g), 5-(2-hydroxyethyl)-1,3,4-thiadiazol-2-thiol (0.97 g.) and sodium bicarbonate (1.01 g.) were dissolved in pH 6.4 phosphate buffer (60 ml.), and the solution was stirred at 60°–65° C for 7 hrs. The reaction mixture was washed with ethyl acetate, and adsorbed on XAD-4 resin (100 ml.) made by Rohm and Haas. The resin was washed with water (1.3 l.) and eluted with methanol (800 ml.). The eluate was treated in a conventional method to give 7-(1H-tetrazol-1-yl)acetamido-3-[5-(2-hydroxyethyl)-1,3,4-thiadiazol-2-yl]thiomethyl-3- cephem-4-carboxylic acid (1.2 g.). m.p. 111°–116° C (dec.).

I.R.: $\nu_{max}^{Nujol}$ cm$^{-1}$: 1760, 1685 max

N.M.R.: δ (DMSO-d$_6$)ppm: 2.92(2H,t, J=5.5Hz), 3.0–3.9(4H,m), 4.20–4.60(2H,m), 5.12(1H,d, J=5Hz), 5.42(2H,s), 5.71(1H,d,d J=5Hz, 8Hz), 9.36(1H,s), 9.55(1H,d, J=8Hz).

EXAMPLE 20

7-(2-Thienyl)acetamido cephalosporanic acid (4.06 g.), 5-hydroxymethyl-1,3,4-thiadiazole-2-thiol (1.48 g.) and sodium bicarbonate (1.76 g.) were dissolved in pH6.4 phosphate buffer (100 ml.), and the solution was stirred at 60° C for 7 hrs. The reaction mixture was washed with ethyl acetate, and the aqueous layer was separated out, adjusted to pH2 with 5% hydrochloric acid, and extracted with ethyl acetate. The extract was washed with a saturated aqueous solution of sodium chloride, and dried over magnesium sulfate, and the solvent was evaporated under reduced pressure to give 7-(2-thienyl) acetamido-3-(5-hydroxymethyl-1,3,4-thiadiazol-2-yl)thiomethyl-3-cephem-4-carboxylic acid (2.6 g.). m.p. 84°–87° C (dec.).

I.R.: $\nu_{max}^{Nujol}$ cm$^{-1}$: 1770, 1710, 1665

N.M.R.: δ (DMSO-d$_6$)ppm: 3.70 (2H, broad s), 3.78 (2H,s), 4.22 (1H,d,J=13Hz), 4.60 (1H,d,J=13Hz), 4.83 (2H,s), 5.09 (1H,d,J=5Hz), 5.69 (1H,d,d,J=5Hz, 8Hz), 6.85–7.42 (3H,m), 9.10 (1H,d,J=8Hz)

EXAMPLE 21

7-(1H-Tetrazol-1-yl)acetamido cephalosporanic acid (2.88 g.), 5-hydroxymethyl-1,3,4-thiadiazole-2-thiol (1.11 g.) and sodium bicarbonate (1.13 g.) were dissolved in pH6.4 phosphate buffer (75 ml.), and the solution was stirred at 60° C for 7 hrs. The reaction mixture was washed with ethyl acetate, adjusted to pH5 with diluted hydrochloric acid and then adsorbed on XAD-4 resin (100 ml.) (made by Rohm and Haas). The resin was washed with water (700 ml.) and eluted with ethanol (600 ml.). The eluate was condensed under reduced pressure to give 7-(1H-tetrazol-1-yl)acetamido-3-(5-hydroxymethyl-1,3,4-thiadiazol-2-yl)thiomethyl-3-cephem-4-carboxylic acid (1.08 g.). m.p. 179°–187° C (dec.).

I.R.: $\nu_{max}^{Nujol}$ cm$^{-1}$: 1750, 1690

N.M.R.: δ (DMSO-d$_6$+D$_2$O)ppm: 3.52(2H, broad s), 4.22(1H,d, J=13Hz), 4.60(1H,d, J=13Hz), 4.77(2H,s), 4.98(1H,d, J=5Hz), 5.34(2H,s), 5.57(1H,d, J=5Hz), 9.30(1H,s)

EXAMPLE 22

Sodium bicarbonate (0.84 g.) and 5-hydroxymethyl-1,3,4-thiadiazole-2-thiol (0.74 g.) were dissolved in water (40 ml.), and the solution was warmed on a water bath. To the solution was added all at once 7-aminocephalosporanic acid (1.36 g.) at 45° C. The mixture was stirred at 70°–73° C for an hour. After the reaction, the reaction mixture was cooled to 0°–5° C and adjusted to pH 5.0 with 10% hydrochloric acid. The precipitating crystals were collected by filtration to give 7-amino-3-(5-hydroxymethyl-1,3,4-thiadiazol-2-yl)thiomethyl-3-cephem-4-carboxylic acid (1.20 g.). m.p. 194°–199° C (dec.)

I.R.: $\nu_{max}^{Nujol}$ cm$^{-1}$: 3200, 1805, 1625

N.M.R.: δ (D$_2$O+DCl)ppm: 3.85 (2H,s), 4.38 (1H,d, J=14Hz), 4.70 (1H,d, J=14Hz), 5.12 (2H,s), 5.20 (1H,d,J=5Hz), 5.38 (1H,d, J=5Hz).

EXAMPLE 23

7-Amino-3-(5-hydroxymethyl-1,3,4-thiadiazol-2-yl)thiomethyl-3-cephem-4-carboxylic acid (1.8 g.) was dissolved in a mixture of water (40 ml.), acetone (40 ml.) and sodium bicarbonate (1.26 g.). On the other hand, 2-(methylthio)acetic acid (1.06 g.) was dissolved in a solution (5 ml.) of thionyl chloride. The solution was stirred at room temperature for 30 minutes, and then at 40°–50° C for 5 minutes. The excess of thionyl chloride was distilled off under reduced pressure. Thus obtained 2-(methylthio) acetyl chloride was dissolved in dried acetone (5 ml.). The acetone solution was added dropwise to the solution obtained above at 0°–5° C for 15 minutes. The mixture was stirred at the same temperature for an hour, and then at room temperature for an hour. From the reaction mixture, the acetone was distilled off under reduced pressure. The residue was washed with ethyl acetate, and then ethyl acetate (200 ml.) was added to the residue. The solution was adjusted to pH 1.5 with 10% hydrochloric acid, and the ethyl acetate layer was separated out. The remaining aqueous layer was extracted with ethyl acetate (100 ml.) four times. The ethyl acetate extracts were put together, washed with a saturated aqueous solution of sodium chloride and dried over magnesium sulfate, and then the solvent was evaporated under reduced pressure to give 7-methylthio acetamido-3-(5-hydroxymethyl-1,3,4-thiadiazol-2-yl)thiomethyl-3-cephem-4-carboxylic acid (1.91 g.) m.p. 134°–139° C (dec.).

I.R.: $\nu_{max}^{Nujol}$ cm$^{-1}$: 3500, 3300, 1780, 1710, 1660

N.M.R.: δ (D$_2$O+NaHCO$_3$) ppm: 2.20 (3H,s,) 3.37 (2H, s), 3.42 (1H,d, J=18Hz), 3.84 (1H,d, J=18Hz), 4.08 (1H,d, J=13Hz), 4.58 (1H,d, J=13Hz), 5.01 (2H,s), 5.14 (1H,d, J=4.5Hz), 5.67 (1H,d, J=4.5Hz)

EXAMPLE 24

7-Methylthioacetamido-3-(5-aminomethyl-1,3,4-thiadiazol-2-yl)thiomethyl-3-cephem-4-carboxylic acid (2.0 g.) was dissolved in a mixture of triethylamine (0.9 g.), water (20 ml.) and tetrahydrofuran (30 ml.). To this solution was added dropwise a solution of acetyl chloride (0.53 g.) in tetrahydrofuran (10 ml.) at 0°–5° C. The mixture was stirred at the same temperature for an hour, and then the tetrahydrofuran was distilled off under reduced pressure. The remaining solution was washed with ethyl acetate (100 ml. ), adjusted to pH1 with 10% hydrochloric acid and then extracted with ethyl acetate (200 ml.). The extract was washed with a saturated aqueous solution of sodium chloride, and the ethyl acetate was evaporated under reduced pressure. The residue was washed with acetone and then with ether to give 7-methylthioacetamido-3-(5-acetamidomethyl-1,3,4-thiadiazol-2-yl)thiomethyl-3-cephem-4-carboxylic acid (1.4 g.). m.p. 145°–150° C (dec.).

I.R.: $\nu_{max}^{Nujol}$ cm$^{-1}$: 3250, 1765, 1705, 1650

N.M.R.: δ (D$_2$O+NaHCO$_3$)ppm:2,10(3H,s), 2.20(3H,s), 3.35(2H,s), 3.40(1H,d,J=18Hz), 3.80(1H,d,J=18Hz), 4.10(1H,d,J=13Hz), 4.55(1H,d,J=13Hz), 4.75(2H,s), 5.15(1H,d,J=5Hz), 5.70(1H,d,J=5Hz)

EXAMPLE 25

7-(2-Thienyl)acetamido-3-(5-aminomethyl-1,3,4-thiadiazol-2-yl)thiomethyl-3-cephem-4-carboxylic acid (2.46 g.) was suspended in methylene chloride (100 ml.). To the suspension was added bis(trimethylsilyl)acetamido (4.06 g.) and the mixture was stirred to give a solution. To the solution was added methanesulfonyl chloride (1.15 g.) and the mixture was stirred at room temperature for 3 hrs. The reaction mixture was added to 5% hydrochloric acid at 0°–5° C. White precipitates in the solution were collected by filtration, dried and then recrystallized with aqueous acetone to give 7-(2-thienyl)acetamido-3-(5-mesylaminomethyl-1,3,4-thiadiazol-2-yl)thiomethyl-3-cephem-4-carboxylic acid (910 mg.). m.p. 139°–145° C (dec.).

I.R.: $\nu_{max}^{Nujol}$ cm$^{-1}$: 3310, 1772, 1720, 1655

N.M.R.: δ (DMSO-d$_6$)ppm:3.00(3H,s), 3.70(2H, broad s), 3.75(2H,s), 4.20(1H,d,J=13Hz), 4.58(1H,d,J=13Hz), 4.57(2H,d,J=6Hz), 5.07(1H,d,J=5Hz), 5.68(1H,d,d,J=5Hz,8Hz), 6.85~7.40(3H,m), 8.07(1H,t,J=6Hz), 9.12(1H,d,J=8Hz)

EXAMPLE 26

N-tert-butoxycarbonylglycine (0.9g.) was dissolved in a solution of triethylamine (0.52 g.) in tetrahydrofuran (20 ml.). To the solution was added dropwise a solution of pivaloyl chloride (0.62 g.) in tetrahydrofuran (6 ml.) under stirring at 0° C, and the mixture was stirred at 0° C for an hour. On the other hand, 7-methylthioacetamido-3-(5-aminomethyl-1,3,4-thiadiazol-2-yl)thiomethyl-3-cephem-4-carboxylic acid (2.0 g.) was dissolved in an aqueous solution (40 ml.) of triethylamine (1.36 g.). To the solution was added all at once the mixed acid anhydride obtained above under stirring at 0° C. The mixture was stirred at 0° C for 30 minutes and then at room temperature for 30 minutes. The tetrahydrofuran was distilled off under reduced pressure from the reaction mixture. The residue was washed with ethyl acetate, adjusted to pH1 with 10% hydro chloric acid and then extracted with ethyl acetate (100 ml.). The extract was washed with a saturated aqueous solution of sodium chloride, dried over magnesium sulfate, and the solvent was distilled off under reduced pressure. The residue was washed with ether to give 7-Methylthioacetamido-3-(5-N-tert-butoxycarbonylglycinamidomethyl-1,3 4-thiadiazol-2-yl)thiomethyl-3-cephem-4-carboxylic acid (2.1 g.). m.p. 90°–95° C (dec.).

I.R.: $\nu_{max}^{Nujol}$ cm$^{-1}$: 1770

N.M.R.: δ(D$_2$O + NaHCO$_3$)ppm:1.38(9H,s), 2.20(3H,s), 3.35(2H,s), 3.45, 3.75(2H,AB-q,J = 18Hz), 3.83(2H,s), 4.1–4.6(2H,m), 4.80(2H,s), 5.15(1H, d,J = 4.5Hz), 5.68(1H,d,J = 4.5Hz)

EXAMPLE 27

7-Methylthioacetamido-3-(5-aminomethyl-1, 3,4-thiadiazol-2-yl)thiomethyl-3-cephem-4-carboxylic acid (2.24 g.) was suspended in water (40 ml.), and triethylamine was added at 0°–5° C to the suspension to give a solution. To the solution was added dropwise for 15 minutes an aqueous solution (30 ml.) of 1-guanidinocarbonylazido (1.92 g.) with keeping the mixture at pH8.6–9.0 by adding triethylamine. The mixture was stirred at 0°–5° C for an hour. The precipitating crystals were collected by filtration, washed with water and then with acetone to give 7-methylthioacetamido-3-[5-(1-guanidino)carbonylaminomethyl-1, 3,4-thiadiazol-2-yl]thiomethyl-3-cephem-4-carboxylic acid (2.62 g.). m.p. 182°–186° C (dec.).

I.R.: $\nu_{max}^{Nujol}$ cm$^{-1}$: 1760, 1725, 1695, 1645, 1600

EXAMPLE 28

7-Methylthioacetamido-3-(5-aminomethyl-1,3, 4-thiadiazol-2-yl)thiomethyl-3-cephem-4-carboxylic acid (1.8 g.) and triethylamine (0.8 g.) was dissolved in a mixture of water (40 ml.) and tetrahydrofuran (40 ml.). A solution of methyl isocyanate (0.46 g.) in tetrahydrofuran (10 ml.) was added dropwise to the solution at 0°–5° C, and the mixture was stirred at the same temperature for 2 hrs. The tetrahydrofuran was distilled off under reduced pressure from the reaction mixture. The residue was washed with ethyl acetate and then adjusted to pH1.0 with 10% hydrochloric acid. The precipitating crystals were collected by filtration and then washed with water to give 7-methylthioacetamido-3-[5-(3-methylureidomethyl)-1, 3,4-thiadiazol-2-yl]thiomethyl-3-cephem-4-carboxylic acid (1.96 g.). The product was suspended in water (50 ml.), and sodium bicarbonate (0.66 g.) was added to the suspension under ice-cooling to give a solution. The insoluble substance was filtered off from the solution, and the solution was adjusted to pH1.0 with 10% hydrochloric acid. The precipitating crystals were collected by filtration, washed with water to give the pure object compound. m.p. 177°–179° C (dec.).

I.R.: $\nu_{max}^{Nujol}$ cm$^{-1}$:3380, 3330, 3250, 1770, 1720, 1670

N.M.R.: δ (D$_2$O + NaHCO$_3$)ppm:220(H3H,s), 2.75(3H,s), 3.38(2H,s), 3.47, 3.77(2H, AB−q,J = 18Hz), 4.12, 4.50(2H,AB−q,J = 13.5Hz), 4.70(2H,s), 5.15(1H,d, J = 4.5Hz), 5.68(1H,d, J = 4.5Hz)

EXAMPLE 29

(1) To a solution of N-acetylglycylhydrazide (52.4 g) in ethanol (1 liter) was added a solution of carbon disulfide (46 g) and potassium hydroxide (40 g) in ethanol (300 ml). The mixture was stirred for 3 hours at 35° to 40° C and allowed to stand overnight at room temperature. The precipitates were collected by filtration and washed with small amount of ethanol to give potassium 3-(N-acetylglycyl)dithiocarbazate (93.4g). m.p. 176° to 178° C.

IR spectrum: ν (Nujol) 1685, 1640 cm$^{-1}$ (2) Potassium 3-(N-acetylglycyl)dithiocarbazate (102.3 g) was added bit by bit to concd. sulfuric acid (1 liter) at 0° to 5° C and the mixture was stirred for an hour at the same temperature. The reaction mixture was added dropwise on crushed ice (c.a. 10 kg) under stirring. Precipitating crystals were collected by filtration to give 5-acetamidomethyl-1,3,4-thiadiazole-2-thiol (54.5 g). m.p. 200° to 203° C.

IR spectrum: ν (Nujol) 3350, 1632 cm$^{-1}$

UV spectrum: $\lambda_{max}^{ethanol}$ 311 mμ

Thus obtained 5-acetamidomethyl-1,3,4-thiadiazole-2-thiol (44 g) was suspended in 6N hydrochloric acid (400 ml) and the mixture was heated to reflux for 2 hours. The reaction mixture was allowed to cool, and the precipitates were collected by filtration and washed with ethanol to give 5-aminomethyl-1,3,4-thiadiazole-2-thiol hydrochloride (28.3 g). m.p. 213° to 217° C. The mother liquid obtained above was concentrated under reduced pressure and the residue was washed with ether to give the same objective product (12.6 g). Total yield is 40.9 g.

NMR spectrum (in D$_2$O): δ(ppm) 4.76 (s)

UV spectrum: $\lambda_{max}^{H_2O}$ 245, 301 mμ, $\lambda_{max}^{NaHCO_3}$ 292.5 mμ

Analysis calculated for $C_3H_5N_3S_2.HCl$ C, 19.62; H, 3.29; N, 22.88; S, 34.91; Cl, 19.30. Found C, 19.64; H, 3.16; N, 23.02; S, 34.76; Cl, 19.38.

EXAMPLE 30

(1) To a solution of N-acetyl-β-alanylhydrazide (7.25 g) and potassium hydroxide (4.95 g) in ethanol (200 ml) was added dropwise carbon disulfide (5.7 g) for about 10 minutes. The mixture was stirred for 3 hours at 35° to 40° C and the precipitate were collected by filtration to give potassium 3-(N-acetyl-β-alanyl)dithiocarbazate (11.8 g). m.p. 173° to 176° C (dec.).

NMR spectrum (in $D_2O$): $\delta_{(ppm)}$ 1.99 (3H,s); 2.58 (2H,t,J = 6Hz); 3.51 (2H,t,J = 6Hz).

(2) Potassium 3-(N-acetyl-β-alanyl)dithiocarbazate (8.15 g) was added bit by bit to concd. sulfuric acid (50 ml) at 5° to 10° C. The mixture was stirred for 30 minutes at the same temperature. The reaction mixture was poured into ice-water (c.a. 300 ml) and adjusted to pH around 6 with 20% sodium hydroxide, and then extracted seven times with ethyl acetate (each 300 ml). The extract was dried and the solvent was distilled off under reduced pressure to give 5-(2-acetamidoethyl)-1,3,4-thiadiazole-2-thiol (5.03 g). having m.p. 157° to 160° C.

IR spectrum: ν (Nujol) 3250, 1625 cm$^{-1}$
UV spectrum: $\lambda_{max}^{phosphate\ buffer\ (ph\ 6.4)}$ 293.5 mµ

Thus obtained 5-(2-acetamidoethyl)-1,3,4-thiadiazole-2-thiol (0.86 g) was dissolved in a mixture of 6N hydrochloric acid (9 ml) and dioxane (5 ml) and the solution was heated to reflux for 2.5 hours. The solvent was distilled off and the residue was washed with ethanol to give 5-(2-aminoethyl)-1,3,4-thiadiazole-2-thiol hydrochloride (700 mg). m.p. 218° to 220° C.

UV spectrum: $\lambda_{max}^{phosphate\ buffer\ (pH\ 6.4)}$ 294 mµ

EXAMPLE 31

(1) To a solution of 3-hydroxypropionylhydrazide (2.08 g) and potassium hydroxide (1.96 g) in ethanol (60 ml), was dropwise added carbon disulfide (2.28 g) for 10 minutes. The mixture was stirred for an hour at 35° to 40° C and then 2 hours at room temperature. The precipitates were collected by filtration to give potassium 3-(3-hydoxypropionyl)dithiocarbazate (4.00 g). m.p. 145° to 148° C (dec.).

(2) Potassium 3-(3-hydroxypropionyl)dithiocarbazate (12 g) was added bit by bit to a mixture of conc. sulfuric acid (15 ml) and ethyl acetate (75 ml) at 0° to 5° C over 15 minutes. The mixture was stirred for an hour at the same temperature. The reaction mixture was poured into ethyl acetate (800 ml), and the organic phase washed with a saturated aqueous solution of sodium chloride and then dried over magnesium sulfate. The solvent was distilled off under reduced pressure to give an oily residue. Petroleum ether was added thereto to solidify and the solid substance was washed with benzene to give 5-(2-hydroxyethyl)-1,3,4-thiadiazole-2-thiol (2.2 g). m.p. 101° to 103° C.

IR spectrum: ν (Nujol) 3280 cm$^{-1}$
UV spectrum: $\lambda_{max}^{phosphate\ buffer\ (pH\ 6.4)}$ 293.5 mµ
NMR spectrum (in DMSO-d$^6$): $\delta_{(ppm)}$ 2.91 (2H, t, J = 6Hz); 3.68 (2H, t, J = 6Hz)

Analysis calculated for $C_4H_6N_2OS_2$: C, 29.61; H, 3.73; N, 17.27; S, 39.53. Found C, 29.62; H, 3.51; N, 17.29; S, 39.90.

EXAMPLE 32

(1) Potassium 3-(1-hydroxyacetyl)dithiocarbazate (15g.) was added gradually over 10 minutes at 0° to 5° C to a mixture of sulfuric acid (20 ml.) and ethyl acetate (100 ml.) and the mixture was stirred for 1 hour at the same temperature. The reaction mixture was poured into ethyl acetate (1 liter) and the mixture was washed with a saturated aqueous solution of sodium and dried over magnesium sulfate. The solvent was distilled off under reduced pressure to give 5-hydroxymethyl1,3,4-thiadiazole-2-thiol (3.7 g). m.p. 120° to 125° C.

UV spectrum: $\lambda_{max}^{ethanol}$ 311 mµ; $\lambda_{max}^{1\%\ NaHCO_3}$ 295 mµ
NMR spectrum (in DMSO-d$^6$): $\delta_{(ppm)}$ 4.57 (s)

Analysis calculated for $C_3H_4N_2OS_2$: C, 24.31; H, 2.72; N, 18.90; S, 43.27. Found C, 24.39; H, 2.66; N, 19.01; S, 43.20.

(2) Isobutyryl chloride (7.9 g) was dropwise added under stirring at 0° to 5° C over 30 minutes to a solution of the above obtained 5-hydroxymethyl-1,3,4-thiadiazole-2-thiol (5.0 g) in pyridine (50 ml). The solution was stirred for further 30 minutes at the same temperature and 2 hours at room temperature. Water (100 ml) was added to the reaction mixture and the mixture was concentrated under reduced pressure on a water bath of 50° C. Cold water (100 ml) was added to the oily residue and sodium bicarbonate (9.3 g) was carefully added under stirring at room temperature to the mixture. After stirring for further 2.5 hours at room temperature, the reaction mixture was washed with ether (discarded), acidified with 10% hydrochloric acid and extracted with ether. The extract was washed with water, dried and evaporated to dryness to give an oily residue (7.7 g). The residue was chromatographed on silica gel (100 g) column developed by a mixture of benzene and chloroform (7:3) to give oil (4.0 g) of 5-isobutyryloxymethyl-1,3,4-thiadiazole-2-thiol.

NMR spectrum (in $CCl_4$): $\delta_{(ppm)}$ 1.23 (6H,d,J = 7 Hz); 2.54 (1H,q,J = 7 Hz); 5.10 (2H,s).

EXAMPLE 33

To a mixture of 5-aminomethyl-1,3,4-thiaziazole-2-thiol hydrochloride (5.5 g) in water (50 ml), dioxane (50 ml) and triethylamine (15 ml) was added t-butoxycarbonyl azide (5.6 g) and the mixture was stirred for 24 hours at 40° to 45° C. After the reaction was over, the dioxane was distilled off under reduced pressure. The residue was adjusted to pH2 with 10% hydrochloric acid and extracted twice with ethyl acetate. The extract was washed with a saturated aqueous soluton of sodium chloride and then dried over magnesium sulfate and then evaporated to dryness to give 5-t-butoxycarbonylaminomethyl-1,3,4-thiadiazole-2-thiol (4.83 g). m.p. 144° to 146° C. IR spectrum: ν(Nujol) 3350, 1675 cm$^{-1}$

We claim:
1. A compound of the formula

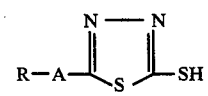

and its pharmaceutically acceptable inorganic acid addition salts, wherein
A is lower alkylene up to six carbons, and
R is amino which may be substituted with lower alkanoyl up to six carbons or lower alkoxycarbonyl up to seven carbons, or
R is hydroxy which may be substituted with lower alkanoyl up to six carbons.

2. A compound according to claim 1 wherein A is methylene and R is acetamido.

3. A compound according to claim 1 wherein A is ethylene and R is acetamido.

4. A compound according to claim 1 wherein A is methylene and R is t-butoxycarbonylamino.

5. A compound according to claim 1 wherein R is amino which may be substituted with lower alkanoyl up to six carbons or lower alkoxycarbonyl up to seven carbons.

6. A compound according to claim 5 wherein A is methylene and R is amino, and its hydrochloride.

7. A compound to claim 5 wherein A is ethylene and R is amino, and its hydrochloride.

8. A compound according to claim 1 wherein R is hydroxy which may be substituted with lower alkanoyl up to six carbons.

9. A compound according to claim 8 wherein A is methylene and R is hydroxy.

10. A compound according to claim 8 wherein A is ethylene and R is hydroxy.

11. A compound according to claim 8 wherein A is methylene and R is isobutyryloxy.

* * * * *

UNITED STATES PATENT OFFICE
CERTIFICATE OF CORRECTION

PATENT NO. : 4,077,965
DATED : March 7, 1978
INVENTOR(S) : Takashi Kamiya et al.

It is certified that error appears in the above-identified patent and that said Letters Patent are hereby corrected as shown below:

Column 6, top formula, change $R_2"$ to read --$R_2'$--;
to the right of the formula add --(I")--.

Column 8, line 8, in formula (IIIa), change "Rq" to --Ra--.

Column 9, line 40, to the right of the formula add --(IXa)--.

Column 11, line 60, in Example 1, change "32" to -- = --.

Column 12, line 20, in Example 2, change "6.10(1H,m)" to read
--6.10 - 6.40(1H,m)--.

Column 16, line 2, change "solubtion" to read --solution--.

Column 16, line 54, change "water" to read --with--.

Signed and Sealed this

First Day of August 1978

[SEAL]

Attest:

RUTH C. MASON
*Attesting Officer*

DONALD W. BANNER
*Commissioner of Patents and Trademarks*